United States Patent
Fukuta et al.

(10) Patent No.: US 7,428,435 B2
(45) Date of Patent: Sep. 23, 2008

(54) MEDICAL INSTRUMENT FOR TRANSDERMALLY ADMINISTERING IONIC MEDICINE

(75) Inventors: Kenji Fukuta, Yamaguchi-ken (JP); Kanji Sakata, Yamaguchi-ken (JP)

(73) Assignee: Tokuyama Corporation (JP)

( * ) Notice: Subject to any disclaimer, the term of this patent is extended or adjusted under 35 U.S.C. 154(b) by 377 days.

(21) Appl. No.: 10/743,947

(22) Filed: Dec. 24, 2003

(65) Prior Publication Data

US 2004/0138609 A1 Jul. 15, 2004

(30) Foreign Application Priority Data

Dec. 26, 2002 (JP) .............................. 2002-376702

(51) Int. Cl.
 *A61N 1/30* (2006.01)
(52) U.S. Cl. ........................................... 604/20
(58) Field of Classification Search ............... 604/20, 604/501, 890.1, 41; 606/41; 607/2, 115, 607/120; 204/533, 632, 633
See application file for complete search history.

(56) References Cited

U.S. PATENT DOCUMENTS

| | | | |
|---|---|---|---|
| 4,217,200 A * | 8/1980 | Kedem et al. | 204/633 |
| 4,713,050 A * | 12/1987 | Sibalis | 604/20 |
| 4,722,726 A | 2/1988 | Sanderson | |
| 5,084,008 A | 1/1992 | Phipps | |
| 5,169,382 A * | 12/1992 | Theeuwes et al. | 604/20 |
| 5,250,022 A | 10/1993 | Chien | |
| 2004/0112752 A1* | 6/2004 | Li et al. | 204/632 |
| 2005/0070840 A1* | 3/2005 | Matsumura et al. | 604/20 |

FOREIGN PATENT DOCUMENTS

| | | |
|---|---|---|
| EP | 0 748 636 | 12/1996 |
| JP | 504343/1991 | 9/1991 |
| JP | 04297277 A | 10/1992 |
| JP | 08098894 A | 4/1996 |
| JP | 2000229128 A | 8/2000 |
| JP | 2000229129 A | 8/2000 |
| JP | 2000 237328 | 9/2000 |
| JP | 2000237328 A | 9/2000 |
| JP | 2000237329 A | 9/2000 |
| WO | WO 90 04433 | 5/1990 |
| WO | WO 90/04433 | 5/1990 |

* cited by examiner

*Primary Examiner*—Kevin C. Sirmons
*Assistant Examiner*—Catherine N Witczak
(74) *Attorney, Agent, or Firm*—H. Jay Spiegel; Robert L. Haines

(57) ABSTRACT

A medical instrument for transdermally administering a medicine, in which an ionic medicine or an ionic medicine-containing substance is sealed in a bag made of an ion-exchange membrane. The medical instrument for transdermally administering the medicine is favorably used for executing the iontophoresis. By using this medical instrument, an iontophoresis device is realized in a simple structure, inexpensively and in a small size, which is suited for being carried yet making it easy to exchange the ionic medicine.

6 Claims, 4 Drawing Sheets

MEDICAL INSTRUMENT FOR TRANSDERMALLY ADMINISTERING IONIC MEDICINE

The present application claims priority to Japanese Patent Application No. 2002-376702, filed on Dec. 26, 2002.

BACKGROUND OF THE INVENTION

1. Field of the Invention

The present invention relates to a medical instrument for transdermally administering an ionic medicine used in the iontophoresis for permeating, into the living body, an ionic medicine useful for the living body by utilizing electrophoresis, and to a portable iontophoresis device by using the above medical instrument.

2. Description of the Related Art

The iontophoresis for permeating, into the living body, an ionic medicine useful for the living body by utilizing the electrophoresis, and has been widely known as a method of administering a medicine of a required amount into a diseased part in a pain-free state.

In the iontophoresis, a medicine-containing layer impregnated with an ionic medicine is placed on the living body, a working electrode is arranged on the side opposite to the living body with the medicine layer sandwiched therebetween, an counter electrode is placed on the living body separated away from the medicine-containing layer, and an electric current is permitted to flow across the working electrode and the counter electrode from a power source causing the ionic medicine to permeate into the living body. So far, this method has used a large device and could be practiced in particular places only such as in a hospital. In order to realize the iontophoresis at any time in any place, therefore, study has been forwarded vigorously concerning the iontophoresis devices that feature simple and compact structures and that can be carried.

The iontophoresis is a method of permeating an ionic medicine into the living body through the living body interface such as skin or mucous membrane. In this method, however, the ionic medicine does not necessarily pass through the living body interface but, conversely, it often happens that sodium cations, potassium cations and chloride anions permeate into the medicine-containing layer from the living body. In particular, ionic medicines that are believed to be useful for the living body have a smaller mobility than those of ions existing in the living body, and a desired medicine is not efficiently administered (does not efficiently permeate into the living body) in proportion to the amount of electricity that is supplied. A proposal has therefore been made to solve the above-mentioned problem by arranging an ion-exchange membrane that permits the passage of ions of the same polarity as the desired ionic medicine between the medicine-containing layer and the living body interface [see, for example, Prior Arts (A) and (B)].

Prior Art (A): International Patent Publication No. 504343/1991

Prior Art (B): Japanese Unexamined Patent Publication (Kokai) No. 98894/1996

However, the iontophoresis device has problems in that the ionic medicine is decomposed on electrodes (working electrode and counter electrode) that are arranged for flowing a current, and water used as a solvent for the ionic medicine undergoes the electrolysis to form $H^+$ ions and $OH^-$ ions that act on the living body to cause inflammation.

In order to solve these problems, a proposal has been made to further arrange an ion-exchange membrane between the medicine-containing layer and the electrode so that the ionic medicine contained in the medicine-containing layer will not come in direct contact with the electrode, and that $H^+$ ions and $OH^-$ ions generated at the electrode will not migrate toward the living body [see, for example, Prior Arts (C) to (G)].

Prior Art (C): Japanese Unexamined Patent Publication (Kokai) No. 297277/1992

Prior Art (D): Japanese Unexamined Patent Publication (Kokai) No. 229128/2000

Prior Art (E): Japanese Unexamined Patent Publication (Kokai) No. 229129/2000

Prior Art (F): Japanese Unexamined Patent Publication (Kokai) No. 237328/2000

Prior Art (G): Japanese Unexamined Patent Publication (Kokai) No. 237329/2000

FIG. 1 illustrates the structure of a representative working electrode part on a conventional iontophoresis device having a plurality of ion-exchange membranes. In FIG. 1, a medicine-containing layer 1 containing an ionic medicine is held in an outer cylinder 2, and an ion-exchange membrane 4 is provided on the side that comes in contact with the surface 3 of the living body for selectively permeating the ions of the same polarity as the pharmacologically effective ions of the ionic medicine. On the side that does not come in contact with the living body, on the other hand, there are arranged an ion-exchange membrane 5 for selectively permeating the ions of the polarity opposite to that of the pharmacologically effective ions of the ionic medicine, as well as an electrolyte layer 6 and an electrode (working electrode) 7 made of gold, platinum, silver or carbon paper. The ion-exchange membranes 4, 5, electrolyte layer 6 and electrode 7 are so held by an inner cylinder 8 as to come in contact with the outer cylinder 2 and the ionic medicine-containing substance (or ionic medicine itself). After the use, a proposal has been made concerning the structure of the working electrode part to remove the inner cylinder 8 and to refill the new medicine-containing layer 1 and the new ion-exchange membrane 5.

However, the above-mentioned conventional structure of the working electrode part is complex holding two pieces of ion-exchange members 4 and 5 in contact with the medicine-containing layer 1. Besides, the outer cylinder 2 and the inner cylinder 8 are the housings that must be made of a material having a strength to some extent. Therefore, the iontophoresis device having the above-mentioned electrode structure is produced through cumbersome steps resulting in an increase in the cost of production. Besides, use of a stiff material deteriorates the property of following the surface 3 of the living body. Further, in order that the medicine-containing layer 1 will not leak out during the transit or preservation, it is necessary to provide all of the ion-exchange membrane 5, electrolyte layer 6, electrode 7 and inner cylinder 8 in place, causing, however, the device to become bulky and heavy, and requiring laborious work and cost for transit and preservation. When the medicine-containing layer 1 is to be renewed, further, the outer cylinder 2 and the inner cylinder 8 that need not be replaced must also be transited. Besides, renewal of the medicine-containing layer 1 requires very cumbersome work, which must be improved.

SUMMARY OF THE INVENTION

It is, therefore, an object of the present invention to provide a medical instrument for transdermally administering an ionic medicine, which is used for an iontophoresis device and permits an ionic medicine to be easily exchanged.

Another object of the present invention is to provide a portable iontophoresis device which is compact and light in weight being equipped with the above-mentioned medical instrument for transdermally administering a medicine.

According to the present invention, there is provided a medical instrument for transdermally administering a medicine comprising a bag made of an ion-exchange membrane, and an ionic medicine or an ionic medicine-containing substance sealed in the bag.

According to the present invention, there is further provided a portable iontophoresis device comprising a medical instrument for transdermally administering a medicine, a working electrode attached to the medical instrument, and a counter electrode electrically connected to the working electrode through a cell.

In the medical instrument for transdermally administering the medicine of the present invention, the ionic medicine or the ionic medicine-containing substance is sealed in the bag made of the ion-exchange membrane. By using the medical instrument for transdermally administering the medicine, therefore, the iontophoresis device becomes very simple in the structure and can be carried. Besides, the medical instrument can be very easily attached to, or detached from, the iontophoresis device. When, for example, the iontophoresis device is to be transited or preserved, the medical instrument is removed. When the iontophoresis device is to be used, the medical instrument is attached thereto to execute the iontophoresis. Further, the medical instrument enables the medicine to be very easily exchanged.

The iontophoresis device equipped with the above medical instrument for transdermally administering the medicine is simple in the structure and can be easily produced, which is advantageous from the standpoint of decreasing the cost yet enabling the ionic medicine to be administered through a flexible membrane which highly follows the surface of the skin.

DETAILED DESCRIPTION OF THE INVENTION

Figure 1:
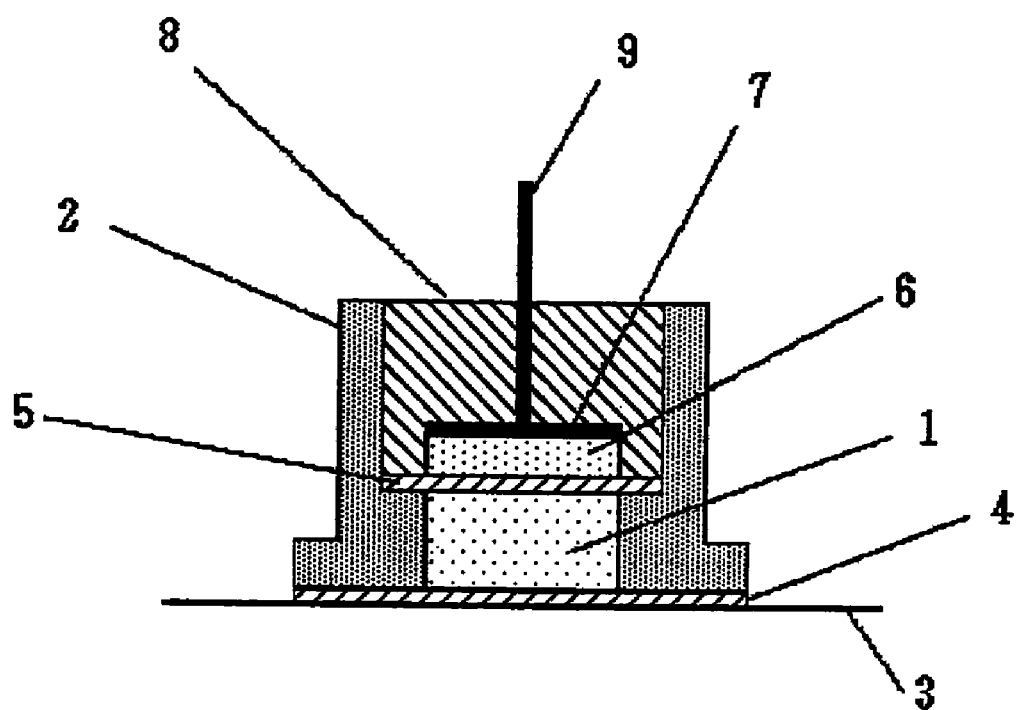
FIG. 1 is a view schematically illustrating the structure of the working electrode part of a conventional iontophoresis device.

The invention will now be described by way of concrete embodiments illustrated in the accompanying drawings, but it should be noted that the invention is in no way limited thereto only. In the drawings, the sizes and angles of some portions are illustrated in an exaggerated manner for easy comprehension of the invention.

Figure 2:
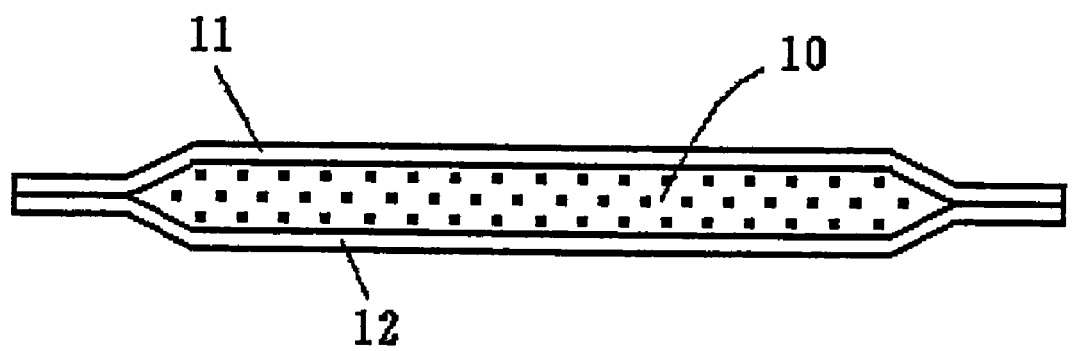
FIG. 2 is a sectional view schematically illustrating a medical instrument for transdermally administering a medicine of the present invention.
Figure 3:
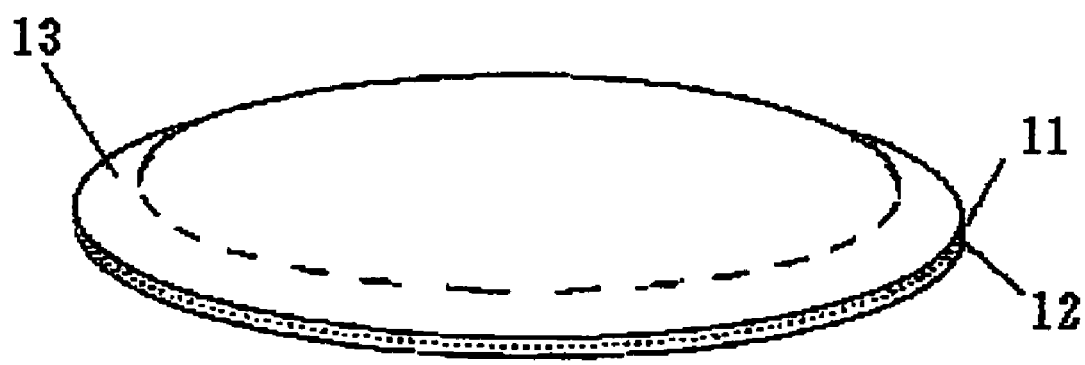
FIG. 3 is a perspective view schematically illustrating the medical instrument for transdermally administering the medicine of the present invention.
Figure 4:
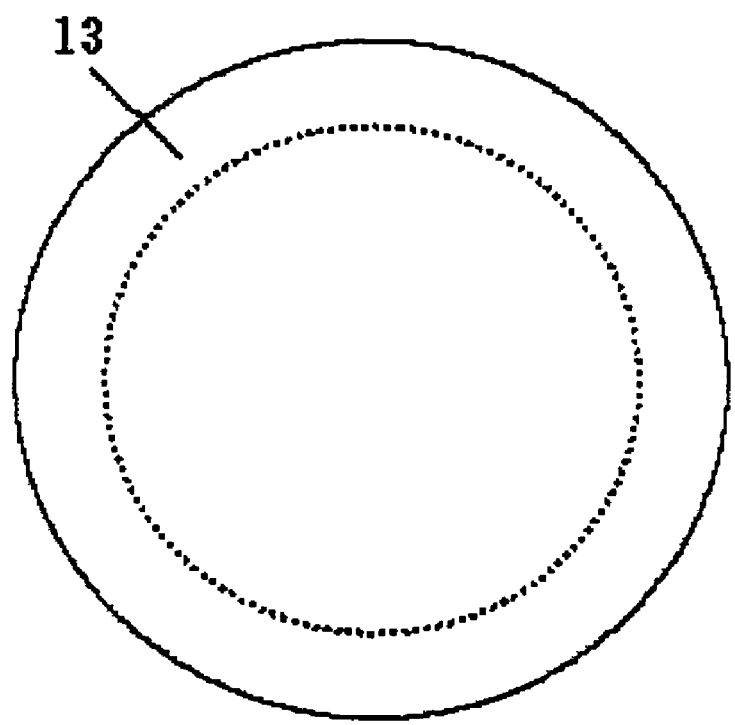
FIG. 4 is a plan view schematically illustrating the medical instrument for transdermally administering the medicine of the present invention.

FIG. 2 is a sectional view illustrating a representative structure of the medical instrument for transdermally administering the medicine of the present invention, FIG. 3 is a perspective view thereof, and FIG. 4 is a plan view thereof.

In FIGS. 2 to 4, an ionic medicine-containing substance (which may be an ionic medicine itself) 10 is contained in a bag obtained by sticking an ion-exchange membrane 11 and an ion-exchange membrane 12 together. The peripheral edge 13 of the bag is sealed over the whole circumference so that the ionic medicine contained therein will not leak out. In FIGS. 3 and 4, the bag has a circular shape in plane but may, as required, have a square shape, a triangular shape or any other shape.

In the medical instrument for transdermally administering the medicine of the present invention having the structure as described above, there is no particular limitation on the ionic medicine provided it is a substance that releases positive ions and negative ions, and exhibits pharmacological effect as the positive ions or negative ions enter into the living body.

Examples of the ionic medicine of which the positive ions exhibit the effect include anesthetics such as procaine hydrochloride, lidocaine hydrochloride and dibucaine hydrochloride; anti-malignant tumor agents such as mitomycin and bleomycin hydrochloride; anodynes such as morphine hydrochloride; steroids such as medroxyprogesterone acetate; histamine and insulin. As the ionic medicine of which the negative ions exhibit the effect, there can be exemplified vitamin compounds such as vitamin B2, vitamin B12, vitamin C, vitamin E and folic acid; anti-inflammatory agents such as aspirin and ibuprofen; adrenocortical hormones such as dexamethasone-type water-soluble compounds; and antibiotics such as benzylpenicillin potassium.

These ionic medicines may be sealed in their own form as the ionic medicine-containing substance 10 in the bag. For easy ionization and for improving permeation efficiency into the living body, however, it is desired that the ionic medicine is used as the ionic medicine-containing substance 10 in a state of being dissolved in a polar solvent such as water or ethanol. For easy production of the medical instrument for transdermally administering the medicine of the invention and for preventing the leakage during the preservation or transit, further, it is desired that the solution of the ionic medicine is maintained in a state having a fluidity as low as possible. To lower the fluidity of the ionic medicinal solution, there can be employed any method that has heretofore been used for the iontophoretic medicines without limitation. For example, there can be used an ionic medicine-containing substance 10 in the form of a paste or a gel by adding hydrophilic polymers, such as polyethylene glycol, polypropylene glycol, polyvinyl alcohol, polyvinyl pyrrolidone or gelatine, or a fine particulate filler such as colloidal silica, to an ionic medicinal solution. It is also allowable to use the one obtained by impregnating a hydrophilic sheet or film with the ionic medicinal solution as the ionic medicine-containing substance 10.

In the present invention, from the standpoint of easily producing the medical instrument for transdermally administering the medicine and very easy handling the instrument, it is desired that the ionic medicine-containing substance 10 is used in the form of a gel, or the hydrophilic sheet or film impregnated with the ionic medicinal solution is used as the ionic medicine-containing substance 10, and that the substance 10 is sealed in a bag of the ion-exchange membranes 11 and 12. Particularly preferably, the hydrophilic sheet or film impregnated with the ionic medicinal solution is used as the ionic medicine-containing substance 10.

As the hydrophilic sheet or film (hereinafter simply called sheet), there can be exemplified papers; cloths such as of cotton, silk and jute; water-absorbing nonwoven papers or nonwoven fabrics; nonwoven papers made of inorganic fibers; crosslinked materials of hydrophilic polymers such as a polyethylene glycol/polypropylene glycol copolymer crosslinked with urethane compound; a thin plate of a hydrophilic inorganic material; and hydrophilic inorganic particles solidified like a sheet. It is desired to use a paper or a nonwoven paper from the standpoint of very easy availability, low cost and self-retaining property and, particularly, to use a filtering paper from such a standpoint that it does not almost contain impurities harmful to the living body.

The ion-exchange membrane 11 and the ion-exchange membrane 12 may be the same or different. From the standpoint of being used for the iontophoresis device, however, it is particularly desired that either one of them is an anion-exchange membrane and the other one is a cation-exchange membrane.

Any known ion-exchange membrane may be used. From the standpoint of easily melt-adhering and sealing the peripheral edge portions, however, it is desired to use the ion-exchange membrane obtained by embedding an ion-exchange resin onto a substrate (such as film or sheet) of a thermoplastic resin. In particular, it is desired to use an ion-exchange membrane obtained by filling part or whole of voids of a porous film of a thermoplastic resin with an ion-exchange resin. By using the thermoplastic resin substrate, the peripheral edges of the two pieces of ion-exchange membranes can be joined together by melt-adhesion to facilitate the production. Further, the porous film has high smoothness on the surface, adheres well, touches well to the surface of the living body, and enables the ionic medicine to be efficiently permeated.

In order to lower the electric resistance of the ion-exchange membrane and to maintain a large mechanical strength, it is desired that the porous film made of the thermoplastic resin has a percentage of voids (also called porosity) of 20 to 95% and, particularly, 30 to 90% and most preferably, 30 to 60%, further, has an air permeance (JIS P-8117) of not longer than 1000 seconds and, particularly, not longer than 500 seconds. It is further desired that the thickness thereof is 5 to 150 µm, particularly, 10 to 120 µm and, more particularly, 10 to 70 µm. To obtain a high close-adhesion to the surface of the living body of when a bag is formed, it is desired that the surface of the porous film has a 10-point height of roughness profile Rz (JIS B 0601-1994) which is as smooth as not larger than 10 µm and, particularly, not larger than 5 µm. As the thermoplastic resin, there can be exemplified polyolefin resins such as polyethylene, polypropylene and polybutene; and vinyl chloride resins such as polyvinyl chloride. From the standpoint of easy melt-adhesion, it is desired to use the polyolefin resin and, particularly, the polypropylene resin or the polyethylene resin.

The porous film can be obtained by the methods described in, for example, Japanese Unexamined Patent Publication (Kokai) Nos. 235399/1997 and 338721/2002. Concretely speaking, the porous film is prepared by mixing an organic liquid to a thermoplastic resin to mold it into a film and, then, extracting the organic liquid from the obtained film by using a solvent. The porous film can be further prepared even by stretching a film of a resin composition obtained by blending the thermoplastic resin with an inorganic filler and/or an organic filler. The porous film is further available in the market in the names of, for example, "Hipore" manufactured by Asahi Kasei Co., "U-Pore" manufactured by Ube Kosan Co., "Setera" manufactured by Tonen Tapils Co., "Exepo" manufactured by Mitsubishi plastics Inc., "Hilet" manufactured by Mitsui Kagaku Co., etc.

The ion-exchange resin filled in the voids of the above porous film has a cation-exchange function or an anion-exchange function, and may be a fluorocarbon-type ion-exchange resin in which ion-exchange groups are introduced into a perfluorocarbon skeleton or may be a so-called hydrocarbon-type ion-exchange resin having, as a skeleton, a resin that has not been fluorinated. From the standpoint of easy production, however, it is desired that the ion-exchange resin is the one of the hydrocarbon type. The filling ratio of the ion-exchange resin in the ion-exchange membrane is, generally, 5 to 95% by weight, preferably, 10 to 90% by weight and, particularly preferably, 20 to 60% by weight for easily permeating the medicinal ions and for improving the strength of the ion-exchange membrane, though the filling ratio may vary depending upon the percentage of voids of the porous film As for the ion-exchange group present in the ion-exchange resin, there is no particular limitation provided it is a functional group capable of forming a group having a negative or positive electric charge in an aqueous solution. As the functional group that could become the ion-exchange group, there can be exemplified the following groups.

Examples of the cation-exchange group include sulfonic acid group, carboxylic acid group and phosphonic acid group. These acid groups may exist in the form of free acids or salts. As the counter cations of the case of salts, there can be exemplified alkali metal cations such as sodium ions and potassium ions, or ammonium ions. Among these cation-exchange groups, it is generally desired to use a sulfonic acid group which is a strongly acidic group.

As the anion-exchange group, there can be exemplified primary to tertiary amino groups, quaternary ammonium group, pyridyl group, imidazole group, quaternary pyridinium group and quaternary imidazolium group. As the counter anions in these anion-exchange groups, there can be exemplified halogen ions such as chlorine ions and hydroxy ions. Among these anion-exchange groups, there are usually used quaternary ammonium group or quaternary pyridinium group which is a strongly basic group.

In the present invention, it is desired that the ion-exchange resin is of the crosslinked type from the standpoint of excellent strength and excellent stability against various solvents.

The ion-exchange membrane having the ion-exchange resin filled in the voids of the porous film can be obtained by a known method without any particular limitation, such as the methods disclosed in Japanese Unexamined Patent Publication (Kokai) Nos. 335473/1999 and 135328/2001. Concretely speaking, the ion-exchange membrane is produced by impregnating the porous film with a monomer which is a precursor of the ion-exchange material such as styrene, α-methylstyrene, vinylnaphthalene, chloromethylstyrene, vinylpyridine or divinylbenzene, and, after polymerization, introducing ion-exchange groups by a known functional group-introduction reaction such as sulfonation or amination.

In the present invention, if it is considered that the medical instrument for transdermally administering the medicine of the above-mentioned structure is used for the iontophoresis, it is desired that the ion-exchange membranes 11 and 12 have an ion-exchange capacity of 0.1 to 6.0 mmols/g, preferably, 0.3 to 4.0 mmols/g, a water content of 5 to 90%, preferably, about 10 to 90%, a fixed ion concentration of 6.0 to 15.0 mmols/g of water, a thickness of 5 to 150 µm, preferably, 10 to 130 µm, and a 10-point height of roughness profile Rz (JIS B 0601-1994) of not larger than 10 µm and, preferably, not larger than 5 µm from the standpoint of permeation efficiency of the ionic medicine into the living body and easiness of production and preservation.

In the medical instrument for transdermally administering the medicine of the present invention, the peripheral edge 13 of the bag (see FIGS. 3 and 4) comprising the ion-exchange membranes 11 and 12 can be sealed without any particular limitation by a method of adhesion using various adhesives, by a method of melt-adhering the thermoplastic resin which is the base material of the ion-exchange membranes by using heat, vibration or high frequency, by a mechanical method of press-adhered sealing by using a clip or the like, or by a combination of the above methods. Among them, however, it is desired to employ a method of sealing by melt-adhesion from the standpoint of easy production, highly retaining the sealed state and small probability of infiltration of impurities into the ionic medicine-containing substance 10. There is no particular limitation on the method of melt-adhesion and any known method may be employed that has been used for melt-adhering the thermoplastic resin film. In general, the melt-adhesion is conducted by pushing a member to the portions where the ion-exchange membranes 11 and 12 are to be joined together to impart a temperature which is higher by 0 to 100° C. than the melting temperature of the thermoplastic resin which is the base material of the ion-exchange membranes 11 and 12, by imparting vibration of 50 to 300 Hz, or by applying a high frequency of 10 to 50 kHz.

There is no particular limitation on the method of producing the medical instrument for transdermally administering the medicine of the present invention, and any method may be employed. For example, a bag having a partly opening portion (mouth) is produced by using the ion-exchange membranes 11 and 12, is filled with the ionic medicine-containing substance 10 and, then, the opening portion is joined and sealed by the above-mentioned means such as melt-adhesion (first method). Or, the ionic medicine-containing substance 10 is sandwiched by two pieces of ion-exchange membranes 11 and 12, and the peripheral edges are joined and sealed at one time (second method).

Figure 5:
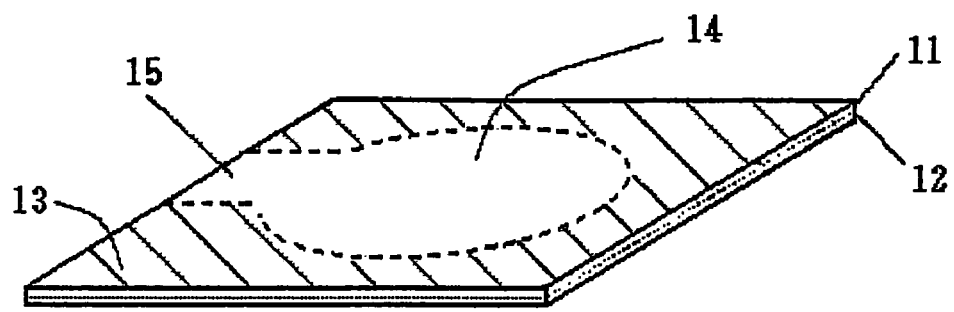
FIG. 5 is a view schematically illustrating a method of producing the medical instrument for transdermally administering the medicine of the present invention.
Figure 6:
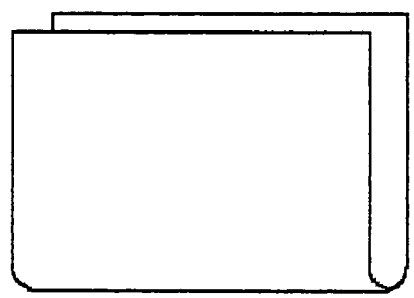
FIG. 6 is a view schematically illustrating another method of producing the medical instrument for transdermally administering the medicine of the present invention.

When the medical instrument for transdermally administering the medicine of the present invention is to be produced by the above first method, as shown in FIG. 5, two pieces of ion-exchange membranes 11 and 12 are overlapped one upon the other, and the peripheral edges 13 thereof are joined together by a heat melt-adhesion or the like method, except the central portion 14 into where the ionic medicine or the ionic medicine-containing substance 10 is introduced and the opening portion 15. Then, the ionic medicine-containing substance 10 is introduced into the bag through the opening portion 15 which is, then, joined by the heat melt-adhesion to obtain the bag that is entirely sealed. Here, when it is desired to obtain a circular bag as shown in FIGS. 3 and 4, or a bag of any other shape, extra portions may be cut simultaneously with the junction of the peripheral portions or after the ionic medicine-containing substance 10 is filled and the mouth portion is sealed. Further, the central portion 14 where the ionic medicine-containing substance 10 is sealed and the ion-exchange membrane used for forming the bag are not necessarily limited to those of the shapes shown in FIG. 5, but may be suitably determined as required. Further, the ion-exchange membranes need not necessarily be those of two pieces that are stuck together. Instead, there may be used a piece of the ion-exchange membrane that is folded as illustrated in FIG. 6.

Figure 7:
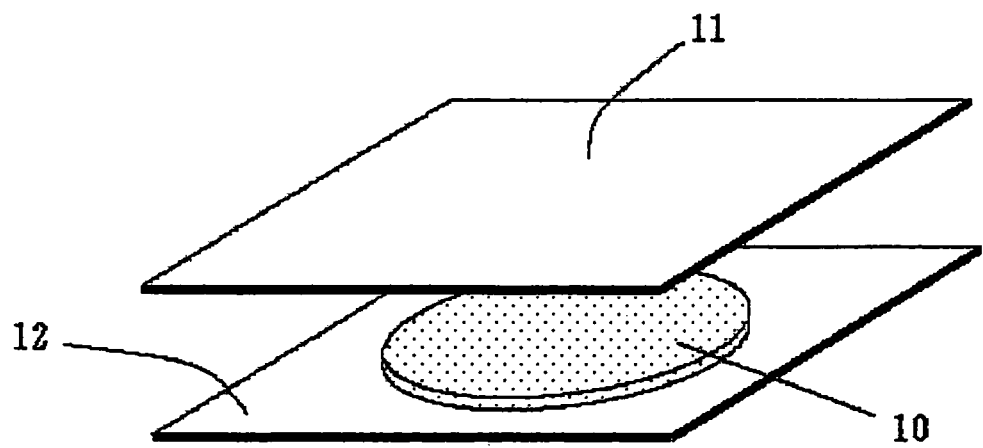
FIG. 7 is a view schematically illustrating a further method of producing the medical instrument for transdermally administering the medicine of the present invention.

When the medical instrument for transdermally administering the medicine of the present invention is to be produced by the above second method as shown in, for example, FIG. 7, the ionic medicine-containing substance 10 is arranged so as to be sandwiched between the two pieces of ion-exchange membranes 11 and 12 which are, then, intimately adhered together. Further, the peripheral edges thereof are joined together by melt-adhesion or the like method, so that the ionic medicine-containing substance 10 is sealed therein. In this case, it is desired to use the ionic medicine-containing substance 10 in the form of a paste or a gel as described earlier, or in the form obtained by impregnating a hydrophilic sheet or film with the ionic medicine so will not to possess self-fluidizing property (does not flow when no stress is imparted). Therefore, the ionic medicine-containing substance 10 does not flow into the portions that are to be joined together, and the production becomes very easy. In particular, use of the ionic medicine-containing substance 10 having shape-retaining property, such as the one obtained by impregnating a gel-like or hydrophilic sheet or film with the ionic medicine, makes it easy to determine the position, which is further desirable. In this case, too, extra portions of the ion-exchange membrane may be cut and removed, as required, to trim the outer shape simultaneously with the junction of the peripheral edges or after the junction has been finished. Further, the ion-exchange membranes 11, 12 and the ionic medicine-containing substance 10 may be suitably determined for their shapes, as required.

In the present invention, the size of the bag formed by using the ion-exchange membranes is not particularly limited but may be suitably determined depending upon the object and use. Generally, however, the diameter in the plane shape thereof or the length of a side thereof is about 0.5 to about 50 cm, and the thickness of the bag is about 40 to about 2300 µm. In this case, the thickness of the ion-exchange membrane itself may be selected to be 5 to 150 µm as descried above and the thickness of the ionic medicine-containing substance 10 may be selected to be 30 to 2000 µm. There is no particular limitation, either, on the size (width) of the peripheral edges for sealing. The size of the peripheral edges may be such that the edges are not easily broken and does not permit the ionic medicine or the ionic medicine-containing substance contained therein to leak out, and may, hence, be suitably determined depending upon the method of sealing or the like. When there is employed the sealing method based on the melt-adhesion of the thermoplastic resin, the width may be, usually, about 0.1 to about 5 mm.

Though there is no particular limitation, the medical instrument for transdermally administering the medicine of the present invention is particularly desirably used for the iontophoresis.

At the time of using the above-mentioned medical instrument for transdermally administering the medicine for the iontophoresis, at least one surface of the bag comprising the ion-exchange membrane is selected to be the ion-exchange membrane for permeating pharmacological ions of the ionic medicine that is sealed therein and, preferably, the opposite surface thereof is selected to be the ion-exchange membrane of the opposite polarity.

Figure 8:
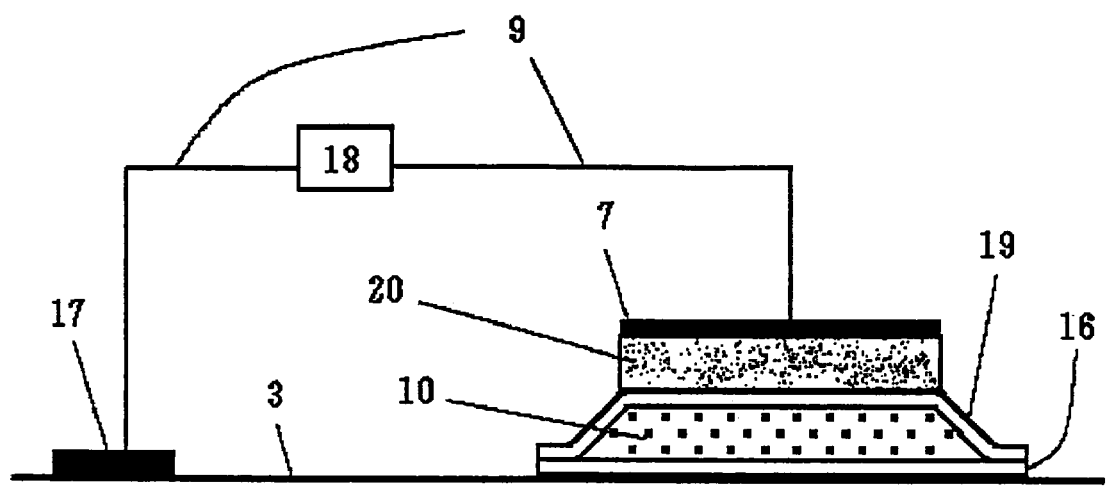
FIG. 8 is a view of concept for illustrating the function of the iontophoresis device by using the medical instrument for transdermally administering the medicine of the present invention.

Referring to FIG. 8 which is a view of concept illustrating the function of the iontophoresis device, the medical instrument for transdermally administering the medicine is so arranged that the ion-exchange membrane 16 for permeating pharmacological ions of the ionic medicine is in contact with the surface 3 of the living body. An electrode (working electrode) 7 is arranged on the ion-exchange membrane 19 on the opposite surface, and is electrically connected, through a conducting wire 9, to a power source 18 and to an electrode (counter electrode) 17 arranged on the surface 3 of the living body. Upon applying a voltage from the power source 18, pharmacological ions of the ionic medicine contained in the ionic medicine-containing substance 10 permeates into the living body. In this case, the electrode (working electrode) 7, conducting wire 9, counter electrode (counter electrode) 17 and power source 18 may be made of materials and in structures that have been known in the art of iontophoresis.

As illustrated in FIG. 8, it is desired that an electrolyte layer 20 is provided between the ion-exchange membrane 19 and the electrode 7 in the medical instrument for transdermally administering the medicine (bag containing the ionic medicine sealed therein). As the electrolyte layer 20, there can be exemplified an aqueous solution of an electrolyte such as sodium chloride, potassium chloride or the like, the one in the form of a paste or a gel obtained by adding the above-mentioned water-soluble polymers to the aqueous solution of the electrolyte, or the one obtained by impregnating a hydrophilic sheet or film with the aqueous solution of the electrolyte.

Figure 9:
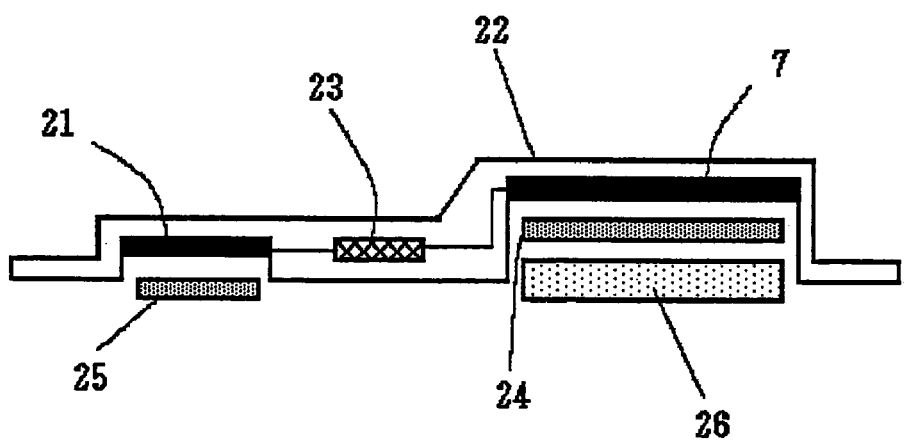
FIG. 9 is a view schematically illustrating the structure of the iontophoresis device by using the medical instrument for transdermally administering the medicine of the present invention.

The structure of the iontophoresis device using the medical instrument for transdermally administering the medicine of the invention will be described below in detail with reference to a schematic view of FIG. 9. In FIG. 9, the electrode (working electrode) 7 and the electrode 21 (electrode counter the working electrode 7) are mounted on a single armoring member 22 at predetermined positions on the inside thereof. The armoring member 22 is made of a highly flexible resin or rubber and exhibits a high degree of follow-up property for the surface (skin) of the living body. The working electrode 7 and the counter electrode 21 are electrically connected to the power source 23 which is a cell such as button cell. An electrolyte layer 24 is provided just under the working electrode 7, and another electrolyte layer 25 is provided just under the counter electrode 21. Under the electrolyte layer 24 which is under the working electrode 7, a space is provided for accommodating the medical instrument 26 for transdermally administering the medicine of the invention (bag of an ion-exchange membrane in which an ionic medicine is sealed). To use the iontophoresis devices, the medical instrument 26 for transdermally administering the medicine and the electrolyte layer 25 are so secured as to be intimately adhered onto the surface of the living body. Then, a current flows, and the pharmacological components in the medical instrument 26 for transdermally administering the medicine permeate into the living body. To prevent a change in the pH of the electrolyte layer 25 under the counter electrode 21 and to prevent the pharmacological ions from oozing out of the living body, it is desired to provide an ion-exchange membrane or a bag of an ion-exchange membrane in which is sealed an electrolyte such as sodium chloride or an electrolyte-containing layer just under the electrolyte layer 25 (between the surface of the living body and the electrolyte layer 25).

When the pharmacological components in the medical instrument 26 for transdermally administering the medicine are all consumed or when it is desired to administer a different medicine, the iontophoresis device itself may be exchanged. It is, further, allowable to remove the medical instrument 26 for transdermally administering the medicine and to replace it by a new one. In this case, the electrolyte layers 24 and 25 can be replaced, as required. To facilitate the replacement, it is desired that the electrolyte layers are in the form of a paste or a gel, or in the state of a solution of an electrolyte being soaked in a filtering paper.

To replace the iontophoresis device itself, the amount of the ionic medicine in the bag constituting the medical instrument 26 for transdermally administering the medicine is so selected as to be the amount that is used each time, and it is desired that the user carries a plurality of iontophoresis devices with him. When the medical instrument 26 for transdermally administering the medicine is to be replaced, further, it is desired that the user carries with him the medical instrument 26 as well as a tube filled with a paste for forming the electrolyte layer 25. Thus, the user (person who needs the medicine administered) is permitted to easily administer the medicine by himself without strict supervision by medical doctors and, hence, to conduct therapy in his home or while he is traveling, which is very advantageous.

According to the medical instrument for transdermally administering the medicine of the present invention, the instrument itself contains and holds the ionic medicine therein, without using a housing for holding the ion-exchange membrane and the ionic medicine, that were so far required by the conventional apparatus. Therefore, the iontophoresis device is realized in a very simple structure so as to follow up the skin to a high degree. Besides, the iontophoresis device can be transited and preserved very easily. Further, after the ionic medicine is administered in a predetermined amount, the medicine can be replaced very easily.

The invention claimed is:

1. A medical instrument for transdermally administering a medicine comprising a bag and an ionic medicine or an ionic medicine-containing substance sealed in the bag, said bag comprising an anion exchange membrane and a cation exchange membrane which are melt-adhered to each other along the peripheral edges thereof, said anion-exchange membrane and said cation-exchange membrane each comprising a film or sheet of a porous thermoplastic resin having a porosity of from 20% to 95%, and a cross-linked ion-exchange resin in the pores of said thermoplastic resin in a filling ratio of from 5% to 95% by weight, wherein said cross-linked ion-exchange resin contained in said cation exchange membrane is a cation-exchange resin and said cross-linked ion exchange resin contained in said anion exchange membrane is an anion-exchange resin.

2. A medical instrument for transdermally administering a medicine according to claim 1, wherein the ionic medicine-containing substance is a sheet or a film impregnated with a solution of an ionic medicine.

3. A medical instrument for transdermally administering a medicine according to claim 1, which is used for the iontophoresis.

4. A portable iontophoresis device comprising a medical instrument for transdermally administering a medicine of claim 1, a working electrode, and a counter electrode electrically connected to the working electrode through a cell, wherein said medical instrument is arranged so that the anion-exchange membrane or the cation-exchange membrane which permeates ions of the same polarity as pharmacologically effective ions of the medicine is capable of coming in contact with a surface of a living body, and the anion-exchange membrane or cation-exchange membrane which permeates ions of a polarity opposite to that of the pharmacologically effective ions of the medicine is connected to the working electrode through an electrolyte layer.

5. A portable iontophoresis device according to claim 4, wherein the working electrode and the counter electrode are mounted on a flexible armoring member.

6. A portable iontophoresis device according to claim 5, wherein the counter electrode is provided with an electrolyte layer in the form of a paste or a gel, and the electrolyte layer and the medical instrument for transdermally administering the medicine are used being in contact with the surface of the living body.

* * * * *